United States Patent [19]

Bergomi et al.

[11] Patent Number: 4,632,988

[45] Date of Patent: Dec. 30, 1986

[54] PROCESS FOR PREPARING N-POLYTHIODIMORPHOLINES

[75] Inventors: Angelo Bergomi, Akron; James J. Tazuma, Stow, both of Ohio

[73] Assignee: The Goodyear Tire & Rubber Company, Akron, Ohio

[21] Appl. No.: 728,915

[22] Filed: Apr. 30, 1985

[51] Int. Cl.$^4$ .......................................... C07D 295/22
[52] U.S. Cl. ...................................... 544/85; 546/186; 564/100
[58] Field of Search ........................................... 544/85

[56] References Cited

U.S. PATENT DOCUMENTS 2,343,524  3/1944  Blake ..................................... 544/85
2,779,761  1/1957  Kibler ..................................... 544/85

Primary Examiner—Robert W. Ramsuer
Attorney, Agent, or Firm—D. O. Nickey

[57] ABSTRACT

This invention relates to a new process for the preparation of N-polythiodimorpholines wherein morpholine and elemental sulfur in an alcohol mixture are oxidized with an alkali metal hypohalite or an alkaline earth metal hypohalite or N-chloromorpholine to yield N-polythiodimorpholines. The process produces N-polythiodimorpholines without the use of corrosive or toxic chemicals and the product is an economical substitute for conventional rubber curatives.

9 Claims, No Drawings

PROCESS FOR PREPARING N-POLYTHIODIMORPHOLINES

TECHNICAL FIELD

The invention relates to a new process for the preparation of N-polythiodimorpholines. The invention provides a product that is in granular form and nearly dust-free. In addition, the process provides for an efficient method of preparing N-polythiodimorpholines that avoids corrosive reaction systems and provides a final product having a high sulfur content.

BACKGROUND

N-polythiodimorpholines have found utility in the rubber industry as sulfur donors and vulcanization accelerators. Previous methods to prepare N-polythiodimorpholines have included adding sulfur to a solution of morpholine disulfide. The problem with this preparation is that the preparation of morpholine disulfide is expensive and cumbersome. Morpholine disulfide is prepared by the reaction of morpholine and sulfur monochloride in the presence of alkali in an organic solvent. M. C. Throdahl and M. W. Harman, Ind. Eng. Chem., 43, 421 (1951).

Another prior art methodology for the preparation of N-polythiodimorpholines involves the use of halopolysulfides and morpholine. This procedure uses the highly toxic and corrosive halopolysulfides, for example, chlorodisulfide and dichloropolysulfides.

There is a need in the rubber chemical industry for a new process that efficiently and economically produces N-polythiodimorpholines which does not require the use of expensive or dangerous starting materials.

DISCLOSURE OF THE INVENTION

There is disclosed a process for the preparation of N-polythiodimorpholines which comprises the steps of: (a) mixing morphololines and sulfur with an alcohol of 1 to 6 carbon atoms, the molar ratio of morpholine to sulfur can range from 1.1:1 to 3.0:1. the amount of alcohol to morpholine and sulfur being at least sufficient to obtain a stirrable reaction mixture; (b) heat the mixture from 60° to 110° C.; (c) to the heated mixture is added an alkali metal hypohalite or an alkaline earth metal hypohalite selected from the group consisting of sodium hypochlorite, sodium hypobromite, sodium hypoiodite, calcium hypochlorite, calcium hypobromite, calcium hypoiodite, potassium hypochlorite, potassium hypobromite, potassium hypoiodite: the molar ratio of sulfur to alkali metal hypohalite can range from 1.5:1 to 2:1: and (d) isolation of the N-polythiodimorpholine product.

More generally, there is disclosed a process for the preparation of N-polythiodiamines wherein a secondary amine and elemental sulfur in an alcohol mixture are oxidized with an alkali metal hypohalite or an alkaline earth metal hypohalite to yield N-polythiodiamines.

There is also disclosed a process for the preparation of N-polythiodimorpholines by the reaction of morpholine with sulfur in the presence of N-chloromorpholine.

Generally, through the process of the instant invention, a mixture of secondary amine sulfides is obtained by the reaction of a secondary amine with sulfur in an alcoholic medium in the presence of an oxidizing agent (bleach) such as sodium hypochlorite. The reaction occurs readily at reflux temperatures. No costly intermediate chemicals are involved and the polysulfides can be obtained in a total selectivity above 85% based on the reacted secondary amine.

Morpholine, a specific starting material for the instant invention has the empirical formula $C_4H_9NO$. It should be appreciated by those skilled in chemistry that the alkyl substituted morpholines, such as 2,6-dimethylmorpholine and heterocyclic aliphatic amines such as piperidine would be suitable for use in the instant invention. In addition, it has been found that the instant process may also use secondary amines such as dimethyl and diethyl amines as a starting material to yield the corresponding polythioamines.

The sulfur used in the instant process is conventional rhombic sulfur that is in the form of a fine powder. Sulfur normally exists in the $S_8$ rombic form, and when used herein, the term "moles of sulfur" actually refers to gram atoms of sulfur. The molar ratio of morpholine to sulfur can range from 1.1:1 to 3.0:1. More preferred is the range of 1.2:1 to 1.5:1. the most preferred range is 1.2:1.

Representative of the alcohols of 1 to 6 carbon atoms useful in the instant process are methanol, ethanol, propanol, isopropanol, butanol, isobutanol, secondary butanol, pentanol, hexanol, and the like. The preferred alcohol for the instant invention is ethanol or isopropyl alcohol.

The amount of alcohol used in the reaction mixture of the morpholine and the sulfur is at least sufficient so as to form a stirrable admixture. Additional amounts of alcohol over that required to form the slurry are not detrimental. However, additional amounts would increase the volume of the admixture to be handled and would require a larger reactor for the same unit of production. It has been found that for approximately every 500 grams of morpholine one liter of alcohol is sufficient.

The mixture of morpholine, sulfur and alcohol is heated to 60°–110° C. It will be appreciated that the process of the instant invention can be conducted at atmospheric or superatmospheric pressures, such as ten atmospheres. In addition, it will be appreciated that the use of superatmospheric pressures with low boiling alcohols at ambient temperature will allow the process to be conducted at temperatures above the boiling point of the alcohol. It has been further found that due to the exothermic nature of the reaction it is advantageous to operate at the reflux temperature of the alcohol so as to facilitate temperature control. More preferred temperature ranges are 70°–90° C., and the most preferred being 75°–85° C. when using isopropyl alcohol as the alcohol.

Representative of the alkali metal hypohalites and alkaline earth metal hypohalites useful in the instant invention are sodium hypochlorite, sodium hypobromite, sodium hypoiodite, calcium hypochlorite, calcium hypobromite, calcium hypoiodite, potassium hypochlorite, potassium hypobromite, and potassium hypoiodite. Of these the most preferred are sodium hypochlorite and calcium hypochlorite.

It should be appreciated that hypohalites other than calcium hypochlorite are not stable in the solid state. Thus, solutions of the other hypohalites would be added to the secondary amine/sulfur/alcohol reaction mixture. The skilled artisan would appreciate that hypohalites such as sodium hypochlorite contain minor amounts of a base as a stabilizer and residuals from the production of the hypohalite. The concentration of the hypohalite solution can range from about 5% to saturation, such as 23% by weight. The more concentrated solutions are preferred since dilute solutions only increase the reaction mixture volume with attendant processing concerns.

It is preferred to add the hypohalite solution to the secondary amine/sulfur/alcohol reaction mixture over a period of time. Addition times of 15 to 45 minutes have been found appropriate.

EXAMPLE 2

As in Example 1, additional runs were conducted wherein the reaction time, the ratios of morpholine to sulfur and the ratios of sulfur to hypohalite were varied. In addition, the alcohols methanol, ethanol and isopropyl alcohol were evaluated. The results from Examples 2–12 are set out in Table I.

TABLE I

| Ex. No. | Time Mins. Incl. Addition | Morpholine gms (moles) | Sulfur gms (moles) | NaOCl moles | Alcohol c.c. | Melting Point °C. | Yield gms. | Disulfide wt. % | Higher Sulfides tri & tetra % wt. |
|---|---|---|---|---|---|---|---|---|---|
| 2 | 45 | 34.6 (0.4) | 6.4 (0.2) | 0.16 | Methanol 100 | 58–70 | 22 | 77 | 20 |
| 3 | 35 | 70 (0.8) | 12.8 (0.4) | 0.236 | Ethanol 200 | 58–64 | 38 | 26 | 70 |
| 4 | 32 | 70 (0.8) | 14 (0.44) | 0.197 | Ethanol 200 | 50–57 | N/A | | 100 |
| 5 | 44 | 70 (0.8) | 15 (0.47) | 0.207 | Methanol 200 | oil | N/A | N/A | N/A |
| 6 | 33 | 70 (0.8) | 12.8 (.4) | 0.227 | Ethanol 150 | 57–67 | 36.5 | 25 | 73 |
| 7 | 36 | 70 (0.8) | 20 (.63) | 0.355 | Ethanol 150 | 48–52 | 58 | 31 | 66 |
| 8 | 34 | 70 (0.8) | 20 (.63) | 0.345 | Isopropyl 150 | 48–72 | 59.4 | 26 | 73 |
| 9 | 70 | 210 (2.4) | 60 (1.9) | 1.064 | Isopropyl 400 | 45–55 | 186 | 23 | 74 |
| 10 | 55 | 420 (4.8) | 120 (3.74) | 2.0 | Isopropyl 1000 | 55–65 | 390 | 20 | 76 |
| 11 | 51 | 420 (4.8) | 154 (4.8) | 2.0 | Isopropyl 1000 | oil | N/A | N/A | N/A |
| 12 | 30 | 84 (0.96) | 35 (1.1) | 0.5 | Isopropyl 100 | paste | N/A | N/A | N/A |
| 13 | 28 | 84 (0.96) | 30 (.94) | 0.51 | Isopropyl 225 | 48–57 | 87 | 15 | 82 |
| 14 | 34 | 420 (4.8) | 120 (3.74) | 2.0 | Isopropyl 1000 | 55–65 | 364 | 22 | 76 |

The molar ratio of sulfur to hypohalite can range from 1.5:1 to 2:1 with 1.7:1 to 1.9:1 being preferred.

The reaction may be carried out batchwise, semicontinuously or continuously in a suitable reactor. It has been found advantageous to continue the reaction after addition of the hypohalite is completed for approximately 5 to 10 minutes.

After the reaction, water is added to dissolve the salt that has precipitated. The mixture is then cooled to ambient temperature and the product crystallizes out which is then separated by filtration. Generally, the reaction product has been found to be a mixture of mono, di, tri and tetra thiodiamines.

An aspect of the present invention is also concerned with the preparation of N-polythiodimorpholines by the reaction of morpholine with sulfur in the presence of N-chloromorpholine.

BEST MODE FOR CARRYING OUT THE INVENTION

The following examples are offered to further illustrate the novelty and utility of the present invention, but not with the intention of unduly limiting the same.

EXAMPLE 1

To a five liter, three necked flask, equipped with a high speed stirrer, condenser, dropping funnel and heating mantel was charged 420 grams of morpholine, 120 grams of sulfur and 1.0 liter of isopropanol. The resultant mixture was stirred vigorously and warmed to reflux (approx. 80° C.) and 1.2 liters of 13% by weight sodium hypochlorite solution was added over a 34 minute interval. The mixture was further reacted and stirred for an additional five minutes. The mixture was chilled and 1.4 liters of distilled water was added. From the chilled mixture, 360 grams of a light, granular product was obtained which had a melting point of 50°–55° C. and was analyzed by HPLC (reverse phase) to consist of 50% by weight trisulfide, 25% by weight disulfide and 25% by weight tetrasulfide dimorpholine.

The results from Table I clearly indicate that through the process of the instant invention, N-polythiodimorpholines can be obtained easily and in good yield.

PIPERIDINE SULFIDES

The procedure described above was followed for the piperidine study (a heterocyclic secondary amine). Piperidine (18.7 gms) and 6.4 gms sulfur were suspended in 100 ml of methanol and heated to reflux. Bleach (100 ml =0.2 moles NaOCl) was added at 65°–75° C. The mixture was then cooled and 200 ml water was added. An oil precipitated. The oil was extracted with ether, washed thoroughly with water and dried over MgSO₄. The ether was then evaporated. The residue (18.0 gms) was an amber oil which had an infrared spectrum very similar to that of piperidine disulfide. Although no detailed analytical data is available, the reaction product appears to be a mixture of piperidine sulfides.

In addition to the hypohalites, N-chloromorpholine can be used as the oxidizing agent for the preparation of polythiodimorpholines. N-chloromorpholine is prepared according to the following procedure:

Preparation of N-Chloromorpholine

Morpholine (87 g, 1 mole) was added at 5° C. with stirring to a solution of 425 ml of 2.6 molar bleach (1.07 moles Na hypochlorite, commercial bleach). After the addition, the cold reaction mixture was transferred into a separatory funnel. The aqueous layer was discarded while the upper layer of N-chloromorpholine was stored at 0° C. over 117.1 g of N-chloromorpholine was recovered.

EXPERIMENTS 15-26

In a typical experiment morpholine, sulfur and potassium carbonate were combined and stirred at 40° C. in 60 ml of methanol. The cold N-chloroporpholine was dissolved in 40 ml of cold methanol and added dropwise over a 90 minute period with stirring. During the addition, the N-chloromorpholine solution was kept at 0°–5° C. to minimize its decomposition. When the addition was completed, the reaction mixture was further stirred for 1 hour at 40° C. cooled to room temperature and then 250 ml cold distilled water was added dropwise. The precipitated product was filtered and dried.

To determine the amount of unreacted sulfur a 5 gm sample was stirred in 100 ml methanol at room temperature for 1 hour. The undissolved product (sulfur) was filtered off, dried, and weighed. The reaction of morpholine with sulfur in the presence of N-chloromorpholine was found to give a mixture of morpholine sulfides. While an excess of morpholine appeared to be beneficial, an excess of N-chloromorpholine was detrimental. In the range explored the ratio of morpholine to sulfur varied from 0.5:1 to 2:1 and the ratio of N-chloromorpholine to sulfur was between 0.5:1 to 1:1. The influence of excess sulfur was also investigated. From the data obtained it appeared that sulfur, when present in excess, had little or no effect on the course of the reaction. Potassium carbonate was used to neutralize the acid formed during the reaction.

The experiments were carried out at 40° C.; although no systematic study of the temperature effect was undertaken, it was found that below 40° C. the reaction was somewhat slow.

In all cases some unreacted sulfur (the amount ranged from traces to 20%) was found in the product. This amount depended upon the reaction conditions. Generally, an excess of morpholine helped in reducing it. Obviously, when an excess of sulfur was used, the amount present at the end was larger.

The results are reported in Table II.

TABLE II

N—CHLORLMORPHOLINE REACTION

| Ex. No. | Morpholine moles* | N—chloro-morpholine, moles | Sulfur, moles | Potassium Carbonate, moles | Recovered Product, g | % Unreacted Sulfur in Product | Melting Point °C. |
|---|---|---|---|---|---|---|---|
| 15 | 0.1 | 0.11 | 0.2 | 0.1 | 12.9 | 20 | 53–94 |
| 16 | 0.2 | 0.22 | 0.2 | 0.1 | 14.2 | 12 | 50–64 |
| 17 | 0.2 | 0.11 | 0.2 | 0.1 | 15.0 | trace | 55–80 |
| 18 | 0.15 | 0.165 | 0.2 | 0.1 | 15.4 | 6 | 50–72 |
| 19 | 0.1 | 0.22 | 0.2 | 0.1 | 11.5 | 14 | 56–70 |
| 20 | 0.2 | 0.165 | 0.2 | 0.1 | 14.4 | 5 | 55–70 |
| 21 | 0.15 | 0.11 | 0.2 | 0.1 | 16.0 | 8 | 53–65 |
| 22 | 0.175 | 0.137 | 0.2 | 0.1 | 15.8 | 6 | 53–65 |
| 23 | 0.4 | 0.11 | 0.2 | 0.1 | 14.8 | trace | 53–73 |
| 24 | 0.4 | 0.22 | 0.2 | 0.1 | 13.7 | trace | 58–84 |
| 25 | 0.15 | 0.11 | 0.3 | 0.1 | 19.1 | 22 | 52–107 |
| 26 | 0.15 | 0.11 | 0.4 | 0.1 | 23.0 | 32 | 53–106 |

All these experiments were performed in methanol at 40° C.

Since an excess of morpholine was found to be advantageous, the unreacted morpholine can be recovered from the reaction mixture with conventional means, such as solvent extraction.

Compounding Study

A compounding study was conducted to compare the products from the process of the instant invention to the known accelerator Sulfasan TM, a 4,4'-dithiodimorpholine supplied by Monsanto. Compounds from Table I were used as a replacement for the conventional vulcanization accelerator in natural rubber, SBR, and nitrile recipes. The study indicated that materials obtained through the process of the instant invention could be used to achieve the same state of cure as the commercially accepted vulcanization accelerator. Overall, the morpholine polysulfides prepared according to the instant invention can be considered competitive with the morpholine disulfides presently used in the industry.

Industrial Applicability

The process of the instant invention fulfills a long-felt need in the rubber chemical industry. The importance of amine sulfides as vulcanization accelerators is well established. See M. C. Throdahl and M. W. Harman, Ind. Eng. Chem. 43, 421 (1951). Through the instant process, N-polythiodimorpholines can be produced efficiently and economically without the use of corrosive or toxic chemicals. Having described the invention in such detail so as to allow one skilled in the art to duplicate the same, the inventors herein claim their invention as follows.

We claim:

1. A process for the preparation of N-polythiodimorpholine wherein morpholine and elemental sulfur in an alcohol mixture are oxidized with an alkali metal hypohalite or an alkaline earth metal hypohalite to yield N-polythiodimorpholines.

2. The process of claim 1 wherein the alcohol is isopropyl alcohol.

3. The process of claim 1 wherein the mixture is heated to 75°–85° C.

4. The process of claim 1 wherein the hypohalite is sodium hypochlorite.

5. The process of claim 1 wherein the alcohol is ethanol.

6. A process for the preparation of N-polythiodimorpholines which comprises the steps of: (a) mixing morpholine and sulfur with an alcohol of 1 to 6 carbon atoms, the molar ratio of morpholine to sulfur can range from 1.1:1 to 3.0:1, the amount of alcohol to morpholine and sulfur being at least sufficient to obtain a stirrable reaction mixture: (b) heat the mixture from 60° to 110° C.: (c) to the heated mixture is added an alkali metal hypohalite or an alkaline earth metal hypohalite selected from the group consisting of sodium hypochlorite, sodium hypobromite, sodium hypoiodite, calcium hypochlorite, calcium hypobromite, calcium hypoiodite, potassium hypochlorite, potassium hypobromite, potassium hypoiodite: the molar ratio of sulfur to hypohalite can range from 1.5:1 to 2:1; and (d) isolation of the N-polythiodimorpholine product.

7. The process of claim 6 wherein the alcohol is isopropyl or ethyl alcohol.

8. The process of claim 6 wherein the admixture is heated to 75°–85° C.

9. The process of claim 6 wherein the hypohalite is sodium hypochlorite.

* * * * *